United States Patent [19]

Mayer

[11] Patent Number: 4,930,532

[45] Date of Patent: Jun. 5, 1990

[54] BEAKER HOLDER FOR USE WITH ULTRASONIC CLEANING DEVICE

[75] Inventor: Stanley E. Mayer, Bronx, N.Y.

[73] Assignee: IPCO Corporation, White Plains, N.Y.

[21] Appl. No.: 312,033

[22] Filed: Feb. 17, 1989

[51] Int. Cl.⁵ .............................................. B08B 3/10
[52] U.S. Cl. ..................................... 134/184; 134/117; 422/300; 366/127; 248/318
[58] Field of Search .......... 134/118, 117, 184; 206/486, 488, 202; 211/74; 366/110, 111, 204, 209, 215, 127; 248/318; 422/297, 300; 68/355

[56] References Cited

U.S. PATENT DOCUMENTS

| | | | |
|---|---|---|---|
| 3,544,073 | 12/1970 | Bodine | 368/113 |
| 3,709,429 | 1/1973 | McKenzie et al. | 211/74 X |
| 3,807,704 | 4/1974 | Janzen | 366/111 |
| 3,842,981 | 10/1974 | Lambert | 211/74 |
| 3,937,236 | 2/1976 | Runnells | 134/184 |
| 4,442,852 | 4/1984 | Lord | 134/184 |

FOREIGN PATENT DOCUMENTS 1456140 11/1976 United Kingdom ................ 134/184

*Primary Examiner*—Frankie L. Stinson
*Attorney, Agent, or Firm*—Helfgott & Karas

[57] ABSTRACT

A holder for a beaker insertable in a container of an ultrasonic cleaning device for cleaning medical or dental tools, dentures, or the like, in a cleaning solution contained in the beaker. The holder includes a ring-shaped member, which receives the beaker and a supporting U-shaped wire which supports the bottom wall of the beaker and is removably-connectable to the ring-shaped member.

28 Claims, 3 Drawing Sheets

4,930,532

BEAKER HOLDER FOR USE WITH ULTRASONIC CLEANING DEVICE

BACKGROUND OF THE INVENTION

The present invention relates to cleaning devices for cleaning medical and dental tools in general, and more particularly to a holder for supporting a beaker immersed in an ultrasonic cleaning device filled with a suitable cleaning liquid.

Ultrasonic cleaning devices for cleaning medical, dental instruments, dentures and the like have been known and typically include a housing with a container which holds a liquid and a transducer to generate and amplify vibrations through the liquid when the transducer is actuated. Medical or dental instruments or dentures are usually placed in a glass beaker in which a cleaning solution is placed. The beaker is then immersed into the container in the ultrasonic cleaning device. Ultrasonic vibrations pass through the liquid in the container and into the beaker. The vibrations shake loose the dirt on the instrument which can then be cleaned within the cleaning solution.

In order to hold the beaker, special templates and baskets have been designed. Typical is that described in U.S. Pat. No. 3,937,236. Since beakers are of different sizes to accommodate various number of and/or various size of medical or dental tools, a great number of such templates having different size openings for receiving the beakers have been required in medical or dental practice.

Furthermore, since the ultrasonic transducer produces standing waves which emanate into the container, it is preferable to space the beaker from the bottom of the container to avoid damping of the standing waves. Likewise, it is preferable to space the beaker from the walls of the container to prevent damping of the ultrasonic waves. In order to hold the beaker in this spaced relationship these templates or holders have included blocks or spacers to space the beaker from the bottom.

All aforedescribed arrangements are complex and time-consuming in use. They have to be assembled before use each time and must be adjusted to accommodate the different beaker sizes.

Accordingly, there is need for a beaker holder easily adjustable to beakers of different sizes and easily and inexpensively manufactured.

SUMMARY OF THE INVENTION

It is an object of the present invention to provide a beaker holder for supporting a beaker in a container of an ultrasonic cleaning device which avoids the aforementioned problems of the prior art devices.

It is another object of the present invention to provide a holder for a beaker containing medical or dental instruments, dentures, or the like, which is easy and inexpensive to make.

Yet another object of this invention is to provide a beaker holder which can be adjusted to different sized beakers.

Still yet a further object of the present invention is to provide a beaker holder which would firmly and reliably support a beaker in a spaced relationship from the bottom of the container of an ultrasonic cleaning device.

Briefly, in accordance with the present invention, there is provided a beaker holder for supporting a beaker within a container filled with a liquid subjected to ultrasonic waves. The beaker holder comprises a ring-shaped member which may typically be made of plastic material, and a metallic wire support member which is detachably-connectable to the ring-shaped member. The holder is inserted in the container of the ultrasonic cleaning device wherein ultrasonic radiation is generated into the liquid in the container. The ultrasonic waves are transmitted through the walls of the container and through the liquid into the beaker in which there is a cleaning solution.

In an embodiment, the ring-shaped member has a split with a circumferential section removed, whereby, the ring-shaped member being flexible, can have its inner diameter adjusted to receive beakers of different diameters.

In an embodiment, inwardly extending spaced-apart projections or tabs are formed on the inner surface of the ring-shaped member. These tabs grip the exterior of the beaker and hold it. Also, they space the beaker from the inner periphery of the ring to accommodate the flow of condensing liquid occurring in the operation of the ultrasonic cleaning device, and feed the liquid back into the container.

In an embodiment, the wire support member is of U-shaped configurations with two vertical legs and a base portion extending therebetween. The wire supports the beaker above the bottom of the container to prevent dampening of the ultrasonic waves at the bottom of the container. The width of the beaker ring itself also serves to space the beaker from the sides of the container to prevent dampening of the waves at the sides of the container.

In an embodiment, two diametrically opposing bent portions extending away from each other are formed on the free ends of the legs of the wire support element. The bent portions are received in L-shaped slots formed in the ring-shaped member to detachably-connect the wire support member with the ring-shaped member.

The aforementioned objects, features and advantages of the invention, will, in part, be pointed out with particularity, and will, in part, become obvious from the following more detailed description of the invention, taken in conjunction with the accompanying drawing, which forms an integral part thereof.

DETAILED DESCRIPTION OF THE PREFERRED EMBODIMENT

Figure 1:
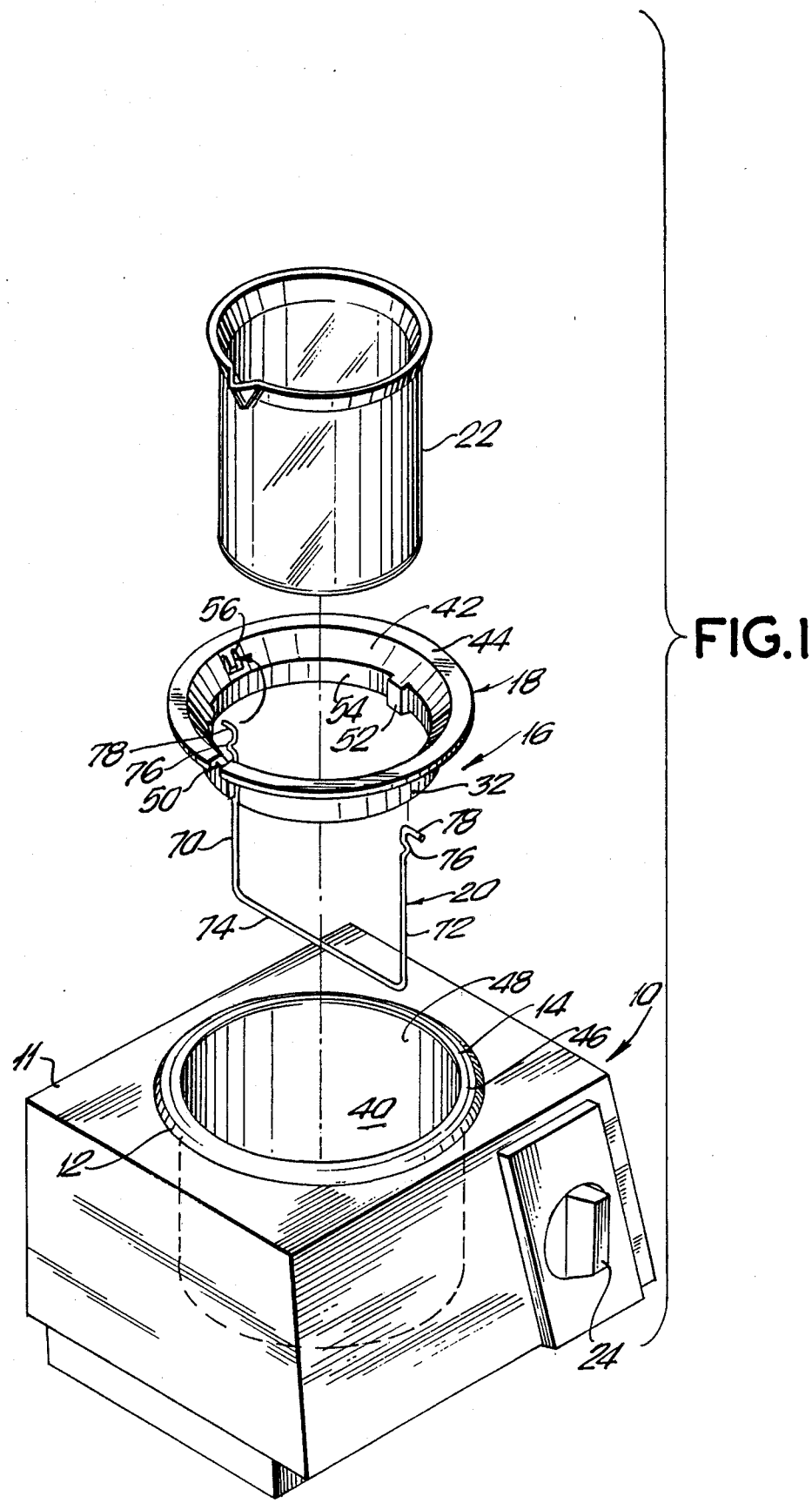
FIG. 1 is an exploded perspective view of the ultrasonic cleaning device with a beaker holder and a beaker according to the present invention.

Referring now to the drawings in detail, FIG. 1 illustrates an ultrasonic cleaning device designated at 10 and including a housing having a top wall 11 having a substantially cylindrical opening 12 which receives a can or container 14 of stainless steel material, or the like, for holding water or any other suitable liquid to which ultrasonic radiation is applied.

A breaker holder 16 is comprised of two easily assembled and disassembled parts, including a substantially ring-shaped holding member 18 and a supporting member 20. A beaker 22 is inserted into the holder 16. The beaker is typically of glass to receive medical or dental instruments, dentures or the like, to be cleaned and also holding a cleaning solution therein.

The ultrasonic vibrations, which produce a cleaning action in the cleaning solution which fills beaker 22, are generated by a transducer and related electrical components arranged in the housing of the ultrasonic cleaning device 10. The transducer and other electrical components for producing the ultrasonic radiation are known and are disclosed in detail, for example in the aforementioned U.S. Pat. No. 3,937,236, the disclosure of which is incorporated herein by reference. The voltage is applied to the non-shown transducer by an operating knob 24 provided on the outer side wall of the housing of the cleaning device 10.

Figure 2:
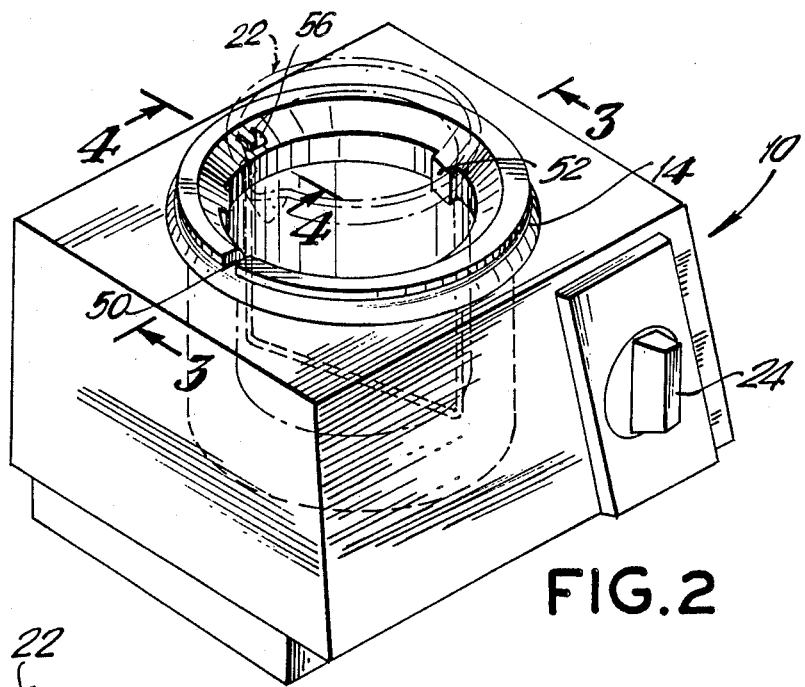
FIG. 2 is a perspective view of the ultrasonic cleaning device with a beaker holder of the present invention inserted therein.

FIG. 2 illustrates the ultrasonic cleaning device with the beaker holder inserted in the container 14 of the cleaning device. The beaker holder sits into the container 14 with a flange of the beaker holder seated on the upper lip of the container. When placed into the holder 16 a bottom side 30 of the beaker 22 rests on the bottom leg of the supporting part 20 of the holder.

Figure 5:
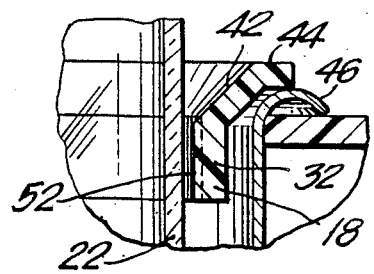
FIG. 5 is an enlarged detail of FIG. 3.
Figure 6:
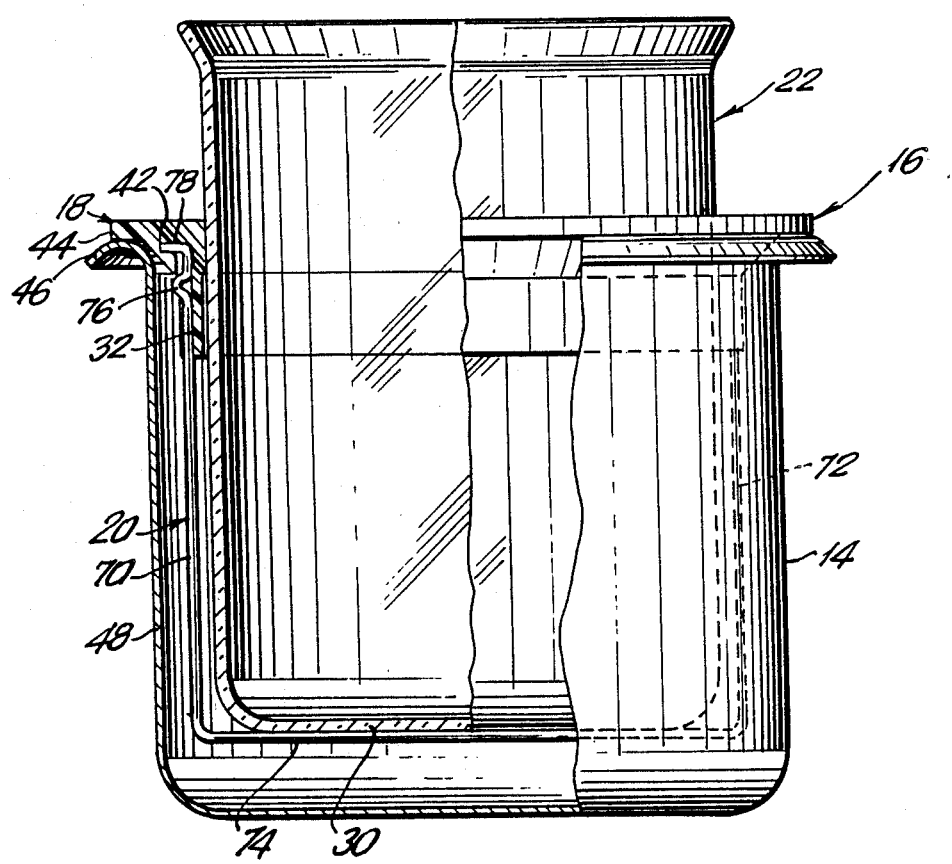
FIG. 6 is an elevational, partially sectional, view of the beaker retained by the beaker holder which is inserted in the container of the ultrasonic cleaning device.

As best seen in FIGS. 1, 5 and 6, the ring-shaped member 18 made of plastic or similar material and includes a substantially cylindrical portion 32, which is received in an internal side wall 40 of the container 14, a frustoconical portion 42 integral with cylindrical portion 32 and merging into a radially outwardly extending flange portion 44 which rests on a lip 46 outwardly protruding from a side wall 48 of the container 14.

The angle of frustoconical portion 42 to the central axis of the ring-shaped member is selected so that the frustoconical portion fits on the edge of the metallic container 14 thus providing a self-centering of the beaker ring in the container.

Ring-shaped member 18 has a circumferential slot 50 which passes through the whole height of the ring-shaped member to provide the beaker ring with the flexibility. In this manner, the beaker holder can expand to adjust to various sizes of beakers being used with the ultrasonic cleaning device. At least three projections 52 circumferentially spaced from each other and protruding inwardly from an inner wall 54 of the cylindrical portion 32 are formed on the ring-shaped member. These projections define gripping members for holding the beaker. Additionally, in the spaces between the inner wall 54 of the ring shaped member and the outer side wall of the beaker 22, there is defined a gap for return flow of condensate formed on the outside of the beaker to flow back into the container.

Figure 3:
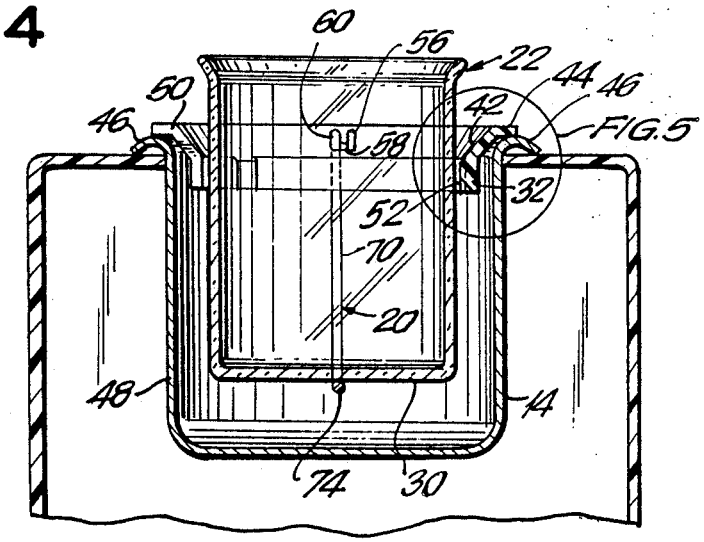
FIG. 3 is a partial sectional view taken along line 3—3 of FIG. 2.

As best seen in FIGS. 1, 2 and 3, two diametrically opposing recesses 56 substantially of U-shape are provided in the inner side of the frustoconical portion 42 of the ring-shaped member. Each recess includes an inverted L-shaped slot or through portion 60 which merges into a vertically extending depression 58 which constitutes the second leg of the U.

Figure 7:
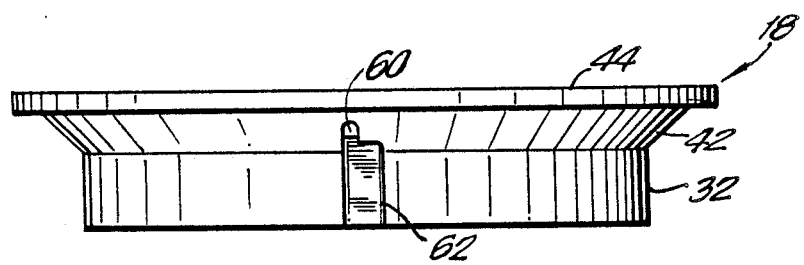
FIG. 7 is a side view of the ring-shaped member of the beaker holder shown in FIG. 6 but turned by 90°.

With reference to FIG. 7 it will be seen that on the outer side of the ring-shaped member two diametrically opposing depressions or recesses 62 are formed corresponding to recesses 56 formed in the oblique or sloped portion 42 of the ring-shaped member. The inverted L-shaped through portion of each recess 56 is seen on the outer side of the frustoconical portion 42 as an L-shaped slot. This slot 60 connects in each case the external recess 62 on the cylindrical portion 32 with the depression 58 formed in the inner wall of the frustoconical portion 42 of the ring-shaped member.

Figure 4:
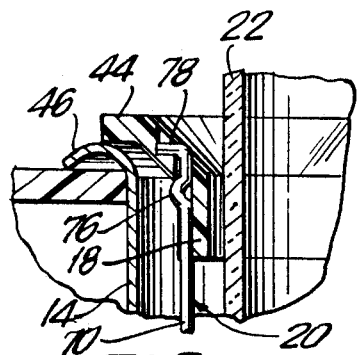
FIG. 4 is a partial sectional view taken on line 4—4 of FIG. 2.

The second or supporting wire 20 of the beaker holder is made of metallic wire and includes two parallel vertical legs 70, 72 (FIGS. 1 and 6) and a base portion 74 interconnecting legs 70 and 72. Base portion 74 receives the bottom of beaker 22 which rests on the base 74 when the supporting wire 20 is snapped into the ring-shaped member 18. Each leg of the supporting wire 20 has an outwardly protruding bulge 76 near the upper end thereof and outwardly extending finger 78 at its upper free end, also shown in FIG. 4.

In assembly, two opposing outwardly extending fingers 78 of vertical legs 70, 72 are inserted through opposing slots 60. By slightly rotating the fingers 78 in the circumferential direction along the inner wall of frustoconical portion 42 of the ring-shaped member, the fingers 78 snap respectively into two opposing depressions 58 so that the two ends of the fingers abut against the base surfaces of these depressions. This shifting motion is aided and limited by outer depressions 62 on which legs 70, 72 slide. When the ends of the fingers 78 are inserted into the respective depressions 58, the vertical movement of legs 70, 72 is additionally limited by bulges 76 each resting against the wall formed by the inverted L-shaped slot 30. The upper portions of legs 70, 72 in this inserted position abut against the base surfaces of outer depressions 62 thus ensuring a reliable bayonet-type connection between the fingers 78 and U-shaped slots 56 of the ring-shaped member. In this manner the supporting wire 20 is firmly held to the ring-shaped member 18.

The supporting wire 20 is of metal and can be flexed. The slot 50 is formed on a wall of the ring-shaped member at a location about half way between the notches 56. As a result, the ring shaped member 18 still maintains its flexibility due to the slot 50 so that the beaker holder can still be adjusted to a beaker of a required size. The wire 20 will just flex outwardly or inwardly as the beaker ring adjusts to the beaker size.

In operation container 14 in the ultrasonic cleaning device is filled with water or any other suitable liquid and the beaker holder 16 with beaker 22 containing a cleaning solution such as a detergent, caustic, acid and the like is placed in the container. Medical or dental tools, dentures or the like to be cleaned therein, is then placed into the beaker 22. As best seen in FIG. 6, the peripheral flange portion 44 of the ring-shaped member 18 rests on the lip 46 of container 14 while the wire support 20 firmly holds the beaker 16 within the container 14. The bottom wall 74 of holder 20 is preferably spaced from the bottom of container 14 by at least the amount equal to the length of a full standing ultrasonic wave. This is to prevent dampening of ultrasonic vibrations. The beaker is also spaced from the walls of the container and avoids dampening of the vibrations. The timer typically provided in the ultrasonic cleaning device is typically set for about 5 to 15 minutes depending on the degree of cleaning required or the voltage applied to the transducer of the ultrasonic cleaning device. The device is switched on by pressing the button or operating knob 24. As known, the cleaning time can be reduced by increasing the voltage applied to the transducer to thereby enhance ultrasonic vibrations. After the cleaning has been completed, the holder 16 with beaker 22 therein is removed from contained 14 and placed on any available drainage tray for rinsing and then sterilization, if needed.

As mentioned above, beakers of various sizes can be easily placed in and held by the holder 16 inasmuch as the diameter of the inner wall of cylindrical portion 32 of the ring-shaped member 18 can be reduced or increased due to slot or cutout 50 through the ring-shaped member. It should be also noted that the distance between two vertical legs 70 and 72 of holder 20 is greater than the outer diameter of the beaker so that the beaker's outer wall is spaced from these legs which also allows for an adjustment to various size beakers.

The holder 16, itself, is easily removable from the cleaning device for cleaning.

There has been disclosed heretofore the best embodiment of the invention presently contemplated. However, it is to be understood that various changes and modifications may be made thereto without departing from the spirit of the invention.

What is claimed is:

1. A beaker holder for supporting a beaker for cleaning medical or dental tools, or the like, in an ultrasonic cleaning device having a liquid-filled container, the holder comprising:
   a ring-shaped member receiving a beaker and having a flange which fits on an edge of the container of the cleaning device; and
   a support member removably-attachable to said ring-shaped member and downwardly depending therefrom and adapted to hold said beaker so that said beaker rests on said support member when the holder is inserted in said container.

2. A beaker holder as in claim 1, wherein said ring-shaped member is provided with means to adjust said ring-shaped member to beakers of different sizes.

3. A beaker holder as in claim 2, wherein said ring-shaped member has a cutout extending therethrough so as to allow said ring-shaped member to flex and accommodate beakers of different sizes.

4. A beaker holder as in claim 2, wherein said ring-shaped member is made of plastic.

5. A beaker holder as in claim 1, wherein said ring-shaped member includes a substantially cylindrical portion through which the beaker passes towards said support member, a frustoconical portion joined with said cylindrical portion, and an outwardly extending flange portion forming said flange and integrally connected with said frustoconical portion and adapted to rest on the edge of said container when said holder is inserted in said container.

6. A beaker holder as in claim 5, wherein said cylindrical portion has an inner wall of a diameter greater than that of the beaker to be received in said ring-shaped member.

7. A beaker holder as in claim 6, wherein a plurality of inwardly extending projections are formed on said inner wall for gripping the beaker, said projections being circumferentially spaced from each other and defining a gap between the inner wall and the beaker which allows a condensing liquid on the beaker to flow back into the container.

8. A beaker holder as in claim 5, wherein said frustoconical portion is inclined to an axis of said ring-shaped member with such an angle that said ring-shaped member is self-centered on the edge of said container.

9. A beaker holder as in claim 1, wherein said support member has such a height that said support member when inserted into said container is spaced from a bottom of said container by at least an amount equal to the length of a full standing ultrasonic wave.

10. A beaker holder as in claim 1, wherein said support member is a wire element.

11. A beaker holder as in claim 10, wherein said wire element is of substantially U-shaped configuration.

12. A beaker holder as in claim 11, wherein said wire element has two parallel vertical legs and a base portion extending therebetween, said beaker when accommodated in said holder resting on said base portion.

13. A beaker holder as in claim 12, wherein said legs have finger portions outwardly extending from said legs in opposite directions.

14. A beaker holder as in claim 13, wherein each leg has an outwardly protruding bulge in the vicinity of a respective finger portion.

15. A beaker holder as in claim 12, wherein a distance between said legs is greater than a diameter of the largest receivable beaker in said ring-shaped member.

16. A beaker holder as in claim 1, further comprising bayonet-type connection means for removably-attaching said support member to said ring-shaped member.

17. A beaker holder as in claim 16, wherein said support member includes a wire element having two parallel legs provided with two finger portions outwardly extending from said legs in opposite directions and a base portion connecting said legs to each other.

18. A beaker holder as in claim 17, wherein said ring-shaped member includes two diametrically opposing slots, said two outwardly extending finger portions being removably insertable into said slots.

19. A beaker holder as in claim 18, wherein each of said slots is L-shaped.

20. A beaker holder as in claim 19, wherein said ring-shaped member has on an inner wall thereof an elongated depression adjacent each L-shaped slot, each finger portion after being inserted into a respective L-shaped slot being shifted circumferentially to rest in a respective elongated depression.

21. A beaker holder as in claim 20, wherein said ring-shaped member includes a substantially cylindrical portion accommodating the beaker, a frustoconical portion joined with said cylindrical portion and a flange portion integral with said frustoconical portion.

22. A beaker holder as in claim 21, wherein said L-shaped slots and each said depression are provided in said frustoconical portion.

23. A beaker holder as in claim 22, wherein said cylindrical portion has in an outer wall thereof two diametrically opposing recesses adjacent said L-shaped slots, said recesses guiding said legs during a shifting motion of said bent portions.

24. A beaker holder as in claim 23, wherein each of said recesses has a base, each of said legs abutting against the base of a respective recess.

25. A beaker holder for supporting a beaker for cleaning medical or dental tools, or the like, in an ultrasonic cleaning device having a liquid-filled container, the holder comprising:
- a ring-shaped resilient member receiving a beaker and having a flange which fits on an edge of said container;
- a wire support member supporting the beaker received in said ring-shaped resilient member at a distance from a bottom of said container; and
- bayonet-type means provided on said ring-shaped member and said wire support member for detachably-connecting said wire support member to said ring-shaped member.

26. A beaker holder as in claim 25, wherein said ring-shaped member has on an inner wall thereof means forming passageway for a return flow of condensing liquid on the outside of the beaker and back into the container.

27. A beaker holder for supporting a beaker for cleaning, medical or dental tools, or the like, in an ultrasonic cleaning device having a liquid-filled container, the holder comprising:
- a ring-shaped member receiving a beaker and adapted to fit on an edge of the container of the cleaning device; and
- a support member removably-attachable to said ring-shaped member and downwardly depending therefrom and adapted to hold said beaker so that said beaker rests on said on support member when the holder is inserted in said container,
said ring-shaped member including a substantially cylindrical portion through which the beaker passes towards said support member, a frustoconical portion joined with said cylindrical portion, and an outwardly extending flange portion integrally connected with said frustoconical portion and adapted to rest on the edge of said container when said holder is inserted in said container.

28. A beaker holder for supporting a beaker for cleaning, medical or dental tools, or the like, in an ultrasonic cleaning device having a liquid-filled container, the holder comprising:
- a ring-shaped member receiving a beaker and adapted to fit on an edge of the container of the cleaning device; and
- a support member removably-attachable to said ring-shaped member and downwardly depending therefrom and adapted to hold said beaker so that said beaker rests on said support member when the holder is inserted in said container, p1 said support member including a wire element having two parallel legs provided with two finger portions outwardly extending from said legs in opposite directions and a base portion connecting said legs to each other,
said ring-shaped member including two diametrically opposing slots, said two outwardly extending finger portions being removably insertable into said slots.

* * * * *